US00PP15803P3

(12) United States Plant Patent
Lintott

(10) Patent No.: US PP15,803 P3
(45) Date of Patent: Jun. 21, 2005

(54) ***CHRYSANTHEMUM* PLANT NAMED 'FOLLIES'**

(50) Latin Name: *Chrysanthemum morifolium*
Varietal Denomination: Follies

(75) Inventor: Keith G. Lintott, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 0 days.

(21) Appl. No.: 10/692,911

(22) Filed: Oct. 24, 2003

(65) Prior Publication Data

US 2004/0083517 P1 Apr. 29, 2004

Related U.S. Application Data

(60) Provisional application No. 60/421,390, filed on Oct. 25, 2002.

(51) Int. Cl.[7] ..... A01H 5/00
(52) U.S. Cl. ..... Plt./292

(58) Field of Search ..... Plt./292

(56) References Cited

PUBLICATIONS

Royal Van Zanten Garden Mum Catalog 2002, listing Chrysanthemum variety 'Follies 'at pages 6 (color picture), 9 and 14, Catalog also lists Chrysanthemum variety 'Nighthawk 'at pages 6 (color picture), 9 and 14.

Royal Van Zanten/Van Zanten Cuttings B.V. 2003–2004 European Catalog, listing Chrysanthemum variety 'Endurance 'at pp. 26–27.

*Primary Examiner*—Anne Marie Grunberg
*Assistant Examiner*—Annette H Para
(74) *Attorney, Agent, or Firm*—Howrey Simon Arnold & White LLP

(57) ABSTRACT

A new variety of *Chrysanthemum* plant named 'Follies,' having a compact round ball shaped habit carrying many small round light purple button type flowers that are very resistant to weather damage.

1 Drawing Sheet

LATIN NAME OF THE GENUS AND SPECIES

Botanical classification: *Chrysanthemum morifolium.*

Variety denomination: The new *Chrysanthemum* variety denomination is 'Follies.'

BACKGROUND OF THE INVENTION

The present invention comprises a new and distinct cultivar of *Chrysanthemum* botanically known as *Chrysanthemum morifolium*, and referred to by the cultivar name 'Follies.'

'Follies,' identified as 31035, originated from a cross made in a controlled breeding program in Chichester, West Sussex, United Kingdom. The female parent of the new variety is the unpatented variety known as 'Endurance.' The male parent of the new variety is an undistributed, unpatented seedling identified as 'G5E6.' The new variety 'Follies' has been asexually reproduced by vegetative cuttings in Chichester, West Sussex, United Kingdom and the distinguishing characteristics are retained through successive generations of asexual reproduction.

BRIEF SUMMARY OF THE INVENTION

'Follies' is a garden type of *Chrysanthemum* plant variety having a domed canopy of small decorative round light purple button type flowers.

Comparison with Parent

Plants of the new *Chrysanthemum* variety 'Follies' are dissimilar to the parent variety 'Endurance' in plant habit and growth rate. In side-by-side comparisons in Chichester, West Sussex, United Kingdom, under commercial practice, plants of the new *Chrysanthemum* variety 'Follies' differed from plants of the parent 'Endurance' in the following characteristics.

1. The new variety 'Follies' produces round light purple button type flowers whereas the parent 'Endurance' produces dark purple flat type flowers.
2. Plants of the new variety 'Follies' have smaller and shorter inflorescence than plants of the parent 'Endurance.'
3. Plants of the new variety 'Follies' are much less vigorous than plants of the parent variety 'Endurance.'

Comparison with Other Varieties

Plants of the new *Chrysanthemum* variety 'Follies' are dissimilar to the unpatented variety 'Nighthawk' in plant habit and growth rate. In side-by-side comparisons in Chichester, West Sussex, United Kingdom, under commercial practice, plants of the new *Chrysanthemum* variety 'Follies' differed from 'Nighthawk' in the following characteristics.

1. The new variety 'Follies' produces smaller and more round flowers than 'Nighthawk.'
2. The new variety 'Follies' has a more compact and shorter habit than 'Nighthawk.'

BRIEF DESCRIPTION OF ILLUSTRATION

Typical specimens of the plant and flowers for the new *Chrysanthemum* variety 'Follies' are shown in the accompanying digital photograph. The colors shown are as true as possible within the usual limits of this kind of illustration.

FIG. 1 is a whole plant view of the new variety 'Follies' grown in a pot. The plant shown in the illustration is 70 days from the commencement of planting outdoors in mid-June.

DETAILED BOTANICAL DESCRIPTION

The following description of the new *Chrysanthemum* variety 'Follies' is of plants grown outside, natural season, in a greenhouse in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 70° F. to 75° F. during the day under natural light conditions. The plants were grown outdoors in mid-June in 4 liter pots using a loamless compost. No growth retardants were used. To produce a commercial product, the plants may be pinched once with the center bud removed. The typical container size for commercial growth is 4 liters (8"). It has been observed that the shelf life of the new variety is about 30 days with a response time of about 9 weeks natural season. The new variety is suitable for growth in a temperature range of 50° F. to 75° F.

The new variety may be produced as a pot plant. The following description is with respect to a plant produced as a garden pot plant. In the description of this new *Chrysanthemum* variety, color values have been taken from The Royal Horticultural Society Colour Chart (R.H.S.C.C.).

Plant

Plant type: Pot.
Habit: Domed — Round.
Height: 35 cm.
Width: 50 cm.
Branching characteristics: Curving — Free Branching.
Length of lateral branches: 8–18 cm.
Number of breaks from pinch: 8–9.
Stem color: Near 137A.
Response time: 63 days natural season.
Vigor: Short/Medium.
Shelf life: Near 30 days.
Disease (susceptibility/resistance observed): None observed to date.
Pest (susceptibility/resistance observed): None observed to date.
Growth retardant type and treatment: No treatment necessary. The plants were grown for 9 weeks in natural season conditions.
Propagation:
- *Type.*—Vegetative propagation via stem cuttings.
- *Time to rooting.*—12 days with soil temperatures of 70° F.
- *Rooting habit.*—Fine and Fibrous.

Foliage

Number of leaves per lateral branch: 7–9.
Compound or single: Single.
Arrangement of leaves: Alternate.
- *Shape of leaf.*—Typically 5 lobed ovate.
- *Size of leaf.*—Width (cm): 1.5–4. Length (cm): 3–5.
- *Leaf apex.*—Acute.
- *Base.*—Truncate.
- *Attachment.*—Petioled.
- *Aspect.*—Slightly Undulating.
- *Margin.*—Palmately Lobed.
- *Surface characteristics.*—Top: Slightly Pubescent. Bottom: Slightly Pubescent.

Petiole:
- *Color.*—Near 138A.
- *Length.*—0.8–1.7 cm.

Venation: Net prominent mid-vein at underside.
- *Color.*—Upper side: Near 138C. Under side: Near 138C.

Color:
- *Mature leaf, upper side.*—Near 137B; under side: Near 137D.
- *Young Leaf, upper side.*—Near 137C; under side: Near 137D.

Flower

Flower appearance: Matte.
Flower type: Decorative.
Flower form: Slightly globular.
Flower shape: Round.
Flowering habit: Cyme.
Number of blossoms per branch: 8–12.
Inflorescence form: Corymibiform.
- *Depth of fully expanded blossoms.*—1.5–2 cm.
- *Diameter of fully expanded blossoms.*—2.5–4 cm.

Phyllaries:
- *Number.*—18–20.
- *Color.*—Near 137B.
- *Length.*—5–9 mm.
- *Width.*—1.5–2 mm.
- *Texture/appearance.*—Shiny and very slightly pubescent.

Pedicel:
- *Length.*—Terminal: 4 cm; lateral: 9 cm.
- *Color.*—Near 136C.
- *Surface.*—Pubescent.
- *Habit.*—Slightly curving.
- *Strength.*—Strong.

Ray florets:
- *Form/shape.*—Gutter shaped, straight.
- *Texture/appearance.*—Matte.
- *Number per flower.*—225–240.
- *Length.*—1–1.5 cm; Width: 4–6 mm.
- *Apex.*—Rounded.
- *Base.*—Tubular.
- *Margin.*—Entire.

Disc florets:
- *Form/shape.*—Cylindrical.
- *Texture/appearance.*—Shiny.
- *Number per flower:* 12–14.
- *Length.*—5–6 mm; Width: <1 mm.
- *Diameter of disc.*—1–2 mm.

Fragrance: None.
Flower bud (at onset of color):
- *Length.*—5–7 mm.
- *Diameter.*—6–8 mm.
- *Form/shape.*—Globular.

General flower color:
1. *Ray florets, upper side.*—Immature: near 58B. Mature: near 58C. Older/Fading: near 58C.
2. *Ray florets, under side.*—Immature: near 58B. Mature: near 58C. Older/Fading: near 58C.
3. *Disc florets.*—Immature: near 58D. Mature: near 58D. Older/Fading: near 58D.
4. *Bud.*—145B.

Flower progression with age: Flowers fade slightly and uniformly with age.

Reproductive Organs

Gynoecium: Present on ray and disc florets.
Ray florets per individual flower:
*Pistil number.*—120–130 observed.
*Stigma color.*—Near 144D.
*Stigma shape.*—Forked.
*Style color.*—Near 144D.
*Style length.*—2–3 mm.
Disc florets per individual flower:
*Pistil number.*—12–14.
*Stigma color.*—Near 150C.
*Stigma shape.*—Forked.
*Style color.*—Near 150C
*Style length.*—2–3 mm. .

Androecium present on Disc florets only:
*Stamen number.*—8 observed.
*Anther shape.*—Cylindrical.
*Anther color.*—Near 14C.
*Pollen color.*—Near 12A.
*Pollen quantity.*—Very little.
Fruit and seeds: None observed.

What is claimed is:

1. A new and distinct variety of *Chrysanthemum* plant, substantially as described and illustrated herein.

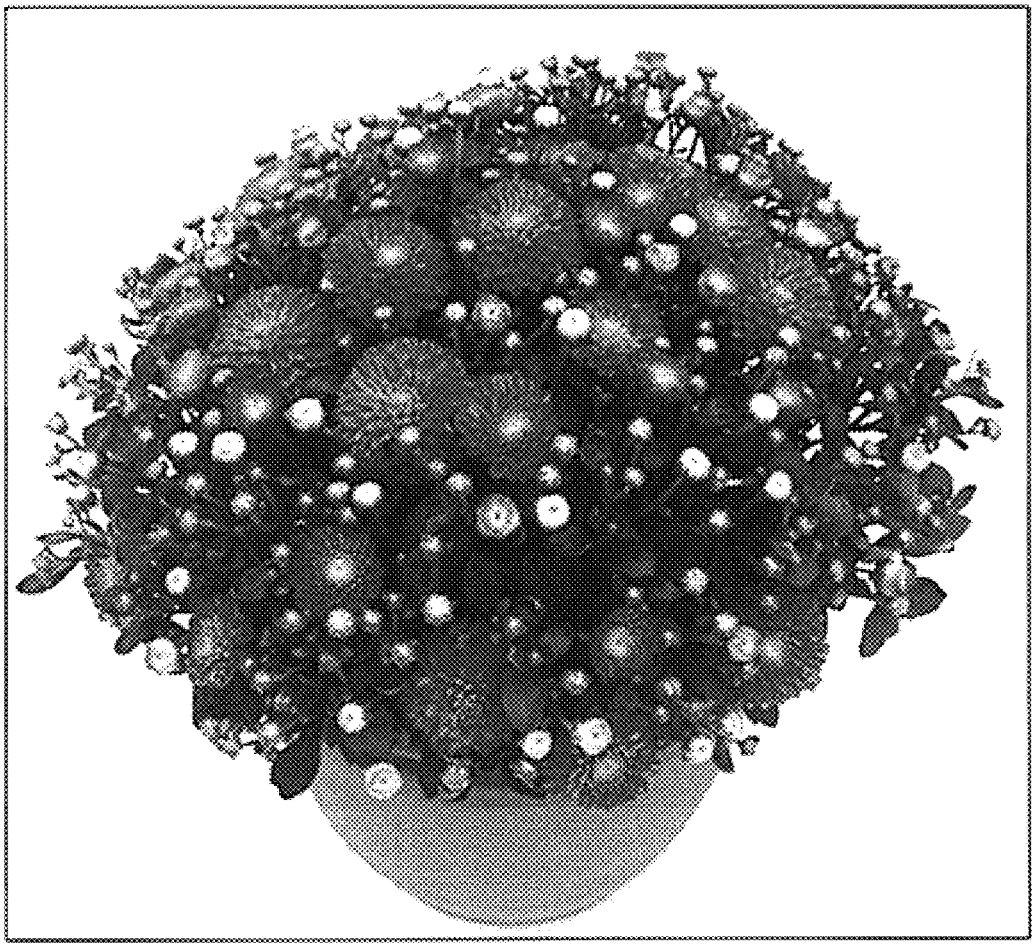

* * * * *